US00PP37776P3

(12) United States Plant Patent
Jones

(10) Patent No.: US PP37,776 P3
(45) Date of Patent: Oct. 13, 2026

(54) ***LEUCANTHEMUM* PLANT NAMED 'LKIWH01-0'**

(50) Latin Name: ***Leucanthemum* x *superbum***
Varietal Denomination: LKIWH01-0

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 19/550,022

(22) Filed: Feb. 25, 2026

(65) Prior Publication Data

US 2026/0271814 P1 Sep. 10, 2026

Related U.S. Application Data

(60) Provisional application No. 63/768,970, filed on Mar. 8, 2025.

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./285
See application file for complete search history.

(56) References Cited

U.S. PATENT DOCUMENTS

PP23,151 P2 * 10/2012 Brown ..... A01H 5/02
Plt./309

* cited by examiner

*Primary Examiner* — Susan Mccormick Ewoldt
*Assistant Examiner* — Zachariah Allan Kay

(57) ABSTRACT

A new and distinct cultivar of *Leucanthemum* plant named 'LKIWH01-0' is disclosed, characterized by very large single flowers (up to 6.5 inches in diameter under ideal conditions). Plants produce flowers equally in both short daylight hours and long daylight hours. Flowers initiate without vernalization. Plants have a wide range of pH tolerance, maintaining leaf color better in warmer conditions making it a desirable retail item. Plants have a short production cycle of The new cultivar is a *Leucanthemum* typically produced as an outdoor ornamental plant.

1 Drawing Sheet

Latin name of the genus and species: *Leucanthemum* x *superbum.*

Variety denomination: 'LKIWH01-0'.

BACKGROUND OF THE INVENTION

The new cultivar is a product of a planned breeding program conducted by the inventor, by open pollination at a nursery in Somis, California. The seed parent is the variety *Leucanthemum*, 'Betsy', unpatented. The pollen parent is unknown. The crossing resulting in the new variety was made during 2020.

The new variety was found and selected by the inventor in July 2021 at the same nursery in Somis, California.

Asexual reproduction of the new cultivar 'LKIWH01-0' was first performed during October of 2021 in Somis, California, by vegetative cuttings. Through subsequent propagation, multiple additional generations have been reproduced, having shown that the unique features of this cultivar are stable and reproduced true to type.

SUMMARY OF THE INVENTION

The cultivar 'LKIWH01-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LKIWH01-0'. These characteristics in combination distinguish 'LKIWH01-0' as a new and distinct *Leucanthemum* cultivar:

1. Very large, single flowers greater than 6.5 inches in diameter in ideal conditions.
2. Flowers without vernalization.
3. Flowers equally well under long and short days for year-round production capabilities.
4. Wider range of pH tolerance, holding leaf color better in warmer conditions making it a more desirable retail item.

PARENT COMPARISON

Plants of 'LKIWH01-0' are similar to plants of the seed parent in most horticultural characteristics, however, plants of 'LKIWH01-0' differ in the following:

1. Flowers of the new variety are larger than flowers of the seed parent.
2. pH tolerance of the new variety is more forgiving in warmer temperatures than the pH tolerance of the seed parent.
3. Plants of the new variety are larger than plants of the seed parent.
4. Leaves of the new variety are darker in warmer temperatures than leaves of the female parent.

COMMERCIAL COMPARISONS

Plants of the new cultivar *Leucanthemum* 'LKIWH01-0' can be compared to the commercial variety *Leucanthemum*

'LWMWH03-0', U.S. Plant Pat. No. 23,151. Plants of 'LKIWH01-0' are similar to plants of 'LWMWH03-0' in most horticultural characteristics, however, plants of 'LKIWH01-0' differ in the following:

1. Flowers of the new variety are much larger than flowers of this comparator.
2. Plants of the new variety are larger than plants of this comparator.
3. Plants of the new variety flower two weeks earlier than plants of this comparator.
4. Plants of the new variety produce more cuttings than plants of this comparator.

BRIEF DESCRIPTION OF THE PHOTOGRAPH

The accompanying photograph illustrates in full color a typical plant of 'LKIWH01-0' grown in a greenhouse in Somis, California. This plant is approximately 1 year old, grown in a 10-inch container.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2015 except where general terms of ordinary dictionary significance are used. The following observations and measurements describe 'LKIWH01-0' plants grown in a greenhouse in Somis, California from August to April. The growing temperature ranged from 15° C. to 16° C. at night to 15° C. to 32° C. during the day. Measurements and numerical values represent averages of typical flowering types.

Botanical classification: *Leucanthemum* x *superbum* 'LKIWH01-0'.

PROPAGATION

Time to Rooting: Approximately 20 days at approximately 20° C.

Root Description: Fine, fibrous.

PLANT

Type: Hardy flowering perennial.

Pot size: 3 gallon.

Height: Approximately 40 cm to top of foliar plane. Approximately 50 cm to top of the highest flower.

Plant Spread: Approximately 50 to 60 cm.

Branching Characteristics: Moderately free branching.

Length of Lateral Branches: Average range 20 to 30 cm.

Diameter of Lateral Branches: 6 to 8 mm.

Quantity of Lateral Branches: Average 2 to 3 per main branch.

Texture of Lateral Branches: Very slightly pubescent, ridged stem.

Color of Lateral Branches: Near RHS Green 137C.

Aspect: Straight.

Internode length: Average 5 cm.

Average number of Leaves per Lateral Branch: Average range 12 to 118.

Age of Plant Described: Approximately 30 weeks from an unrooted cutting.

FOLIAGE

Leaf:

*Arrangement.*—Alternate, simple.

*Average length.*—Average range 8 to 12 cm.

*Average width.*—Average range 2.5 to 3.0 cm.

*Shape of blade.*—Oblanceolate.

*Apex.*—Acute.

*Base.*—Truncate.

*Attachment.* Sessile.

*Margin.*—Dentate.

*Texture of top surface.*—Smooth.

*Texture of bottom surface.*—Smooth. Occasionally slightly pubescent along mid-vein.

*Leaf internode length.*—Average range 2.5 cm to 5 cm.

*Color.*—Young foliage upper side: Near RHS Green 137A. Young foliage under side: Near RHS Green 137B. Mature foliage upper side: Near RHS Green 137A. Mature foliage under side: Near RHS Green 137B.

*Venation.*—Type: Pinnate. Venation color upper side: Near RHS Green 138B. Venation color under side: Near RHS Green 138B.

FLOWER

Bloom Period: Naturally blooming from Spring to early Fall.

Bud:

*Bud shape.*—Flattened sphere.

*Bud length.*—Approximately 9 mm.

*Bud diameter.*—Approximately 22 mm.

*Bud color.*—Near RHS Green 137C.

Inflorescence:

*Quantity per plant.*—Average range around 10 to 15 open inflorescences on a plant in a 3 gallon pot at full bloom.

*Form.*—Simple composite daisy. Inflorescences occurring mainly on upright terminal peduncles, pinching promotes flowering on lateral peduncles.

*Lastingness of inflorescence.*—Approximately 3 weeks in good condition, from fully opened.

*Diameter of entire inflorescence.*—Average range 8 to 16 cm.

*Depth of inflorescence.*—Approximately 1.4 cm.

*Width of disc.*—Average range 1.5 to 3 cm.

*Depth of disc.*—Approximately 1.4 cm.

Receptacle:

*Shape.*—Shallow dome.

*Width.*—1.5 cm.

*Depth.*—0.5 cm.

*Color.*—Near RHS Yellow-Green 145C.

Ray Florets:

*Number of Ray Florets.*—Average 40, arranged in a single or double whorl.

*Length.*—Average range 4.5 to 8 cm.

*Width.*—Approximately 10 mm.

*Apex.*—3 or 4 very shallow irregularly rounded lobes.

*Base.*—Attenuate.

*Shape.*—Oblanceolate.

*Margin.*—Entire.

*Texture.*—Smooth all surfaces.

*Aspect.*—Flat.

*Color.*—Upper surface at first opening: Near White RHS 155C, small basal section colored Green 143B. Upper surface at maturity: Near RHS White 155C small basal section colored. Green 143B. Upper surface at fading: Near RHS White 155C, small basal section colored Green 143C. Under surface at first opening: Near RHS White 155C, small basal section colored Green 143B. Under surface at maturity: Near RHS White 155C small basal section colored Green 143B. Under surface at fading: Near RHS White 155C, small basal section colored Green 143C.

Disc Florets:

*Number.*—About 300.

*Length.*—Average 7 mm.

*Width.*—Base about 2 mm, apex can flare to 3 mm wide.

*Apex.*—Acute.

*Shape.*—Cylindric.

*Margin.*—Entire.

*Color.*—At first opening: Base near RHS Green 143C, apex near Yellow 12B flushed Green-Yellow 1B. At maturity: Base near RHS Green 143C, apex near Yellow-Orange 17B. At fading: Base near RHS Yellow-Green 145C, apex near Yellow 6B.

Fragrance: Moderate to faint grassy scent.

Involucral bracts/phyllaries:

*Number.*—Approximately 60 to 70 in 3 to 4 very tightly held rows.

*Length.*—Approximately 11 to 15 mm.

*Width.*—Approximately 4 to 5 mm.

*Shape:.*—Lanceolate.

*Apex.*—Broad acute.

*Base.*—Attenuate.

*Margin.*—Entire, membranous.

*Texture.*—Glabrous all surfaces.

*Color.*—Inside surface: Near RHS Green 137C. Outside surface: Near RHS Green 137A.

Peduncle:

*Length.*—Average 6 cm.

*Width.*—Approximately 6 mm.

*Texture.*—Ridged, slightly pubescent.

*Color.*—Near RHS Green 137A.

REPRODUCTIVE ORGANS

Androecium: Present in disc florets only.

*Stamens.*—4.

*Anther length.*—Approximately 0.5 mm.

*Anther color.*—Near RHS Yellow 13A.

*Pollen color.*—Scant colored near RHS Yellow 13B.

Gynoecium: Present on ray and disc florets.

Ray Florets:

*Number of pistils per flower.*—1.

*Pistil length.*—About 4 mm.

*Stigma shape.*—Two parted.

*Stigma color.*—Near RHS Yellow 12A.

*Style color.*—Near RHS Green-White 157D.

*Style length: Approximately* 2 mm.

Disc Florets:

*Number of pistils per flower.*—1.

*Stigma shape.*—Two parted.

*Stigma color.*—Near RHS Yellow-Orange 17A.

*Style color.*—Near RHS Green-Yellow 1C.

*Style length.*—Approximately 2 mm.

OTHER CHARACTERISTICS

Disease and pest resistance: Neither resistance nor susceptibility to diseases or pests has been observed in this variety to date.

Temperature tolerance: Hardy perennial. Hardy to at least −2° C., high temperature tolerance to at least 35° C.

Fruit/seed production: Fruit and seed production have not been observed in the new cultivar.

What is claimed is:

1. A new and distinct cultivar of *Leucanthemum* plant named 'LKIWH01-0' as herein illustrated and described.

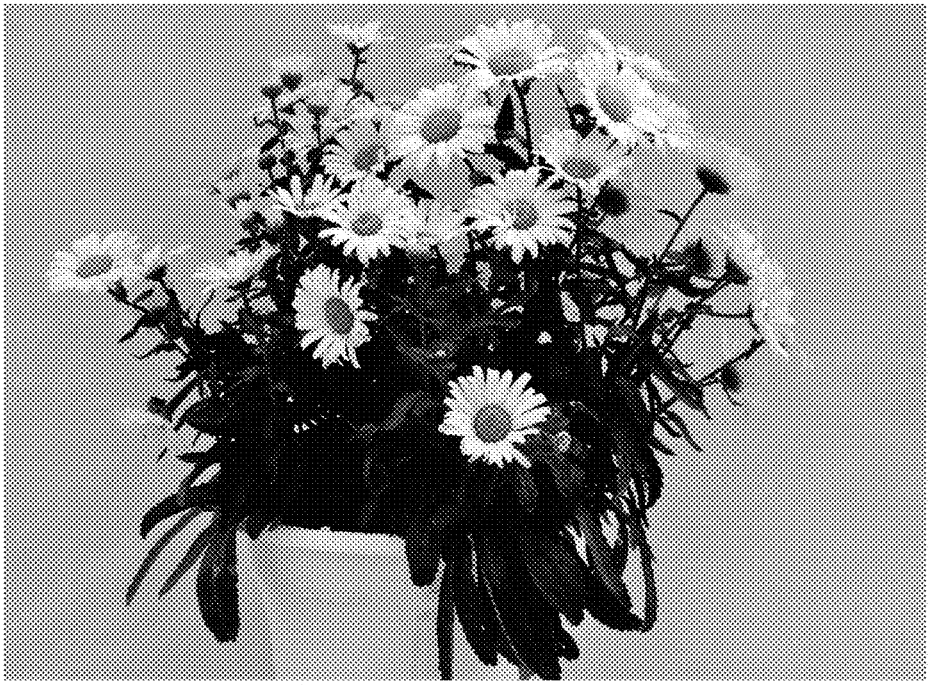

* * * * *